United States Patent
Graf

(10) Patent No.: US 9,309,476 B2
(45) Date of Patent: Apr. 12, 2016

(54) PROCESS FOR OBTAINING HIGHLY PURE METHANE FROM BIOGAS, AND PLANT FOR CARRYING OUT THE PROCESS

(71) Applicant: Lukas Graf, Stuttgart (DE)

(72) Inventor: Lukas Graf, Stuttgart (DE)

(73) Assignee: EISENMANN AG, Boeblingen (DE)

( * ) Notice: Subject to any disclaimer, the term of this patent is extended or adjusted under 35 U.S.C. 154(b) by 0 days.

(21) Appl. No.: 14/203,875

(22) Filed: Mar. 11, 2014

(65) Prior Publication Data

US 2014/0251128 A1 Sep. 11, 2014

(30) Foreign Application Priority Data

Mar. 11, 2013 (DE) .......................... 10 2013 004 079

(51) Int. Cl.
*B01D 53/22* (2006.01)
*C10L 3/10* (2006.01)
*C12M 1/00* (2006.01)

(52) U.S. Cl.
CPC ................. *C10L 3/10* (2013.01); *B01D 53/226* (2013.01); *C10L 3/104* (2013.01); *C12M 47/18* (2013.01); *B01D 2256/245* (2013.01); *B01D 2258/05* (2013.01); *C10L 2290/26* (2013.01); *C10L 2290/46* (2013.01); *C10L 2290/548* (2013.01); *C10L 2290/58* (2013.01); *C10L 2290/60* (2013.01); *Y02E 50/343* (2013.01); *Y02P 20/59* (2015.11)

(58) Field of Classification Search
CPC ................. B01D 53/22; B01D 53/226; B01D 2256/245; B01D 2258/05; B01D 2317/02; B01D 2317/022; B01D 2317/025; C10L 3/10; C10L 3/101; C10L 3/104; C10L 2290/26; C10L 2290/46; C10L 2290/548; C10L 2290/58; C10L 2290/60; C12M 47/18; Y02E 50/343

USPC ................................. 95/8, 47, 49, 51; 96/4, 9
See application file for complete search history.

(56) References Cited

U.S. PATENT DOCUMENTS

| | | | | |
|---|---|---|---|---|
| 5,053,058 A | * | 10/1991 | Mitariten | 95/8 |
| 5,281,253 A | * | 1/1994 | Thompson | 95/22 |
| 8,454,724 B2 | * | 6/2013 | Sharma et al. | 95/8 |

(Continued)

FOREIGN PATENT DOCUMENTS

| | | |
|---|---|---|
| DE | 10 2008 032 864 A1 | 1/2010 |
| DE | 10 2010 003 507 A1 | 10/2011 |

(Continued)

*Primary Examiner* — Jason M Greene
(74) *Attorney, Agent, or Firm* — Factor Intellectual Property Law Group, Ltd.

(57) ABSTRACT

A process and a plant for obtaining highly pure methane from biogas where biogas coming from a fermenter is compressed and fed to at least one membrane unit having a selectively permeable membrane, which provides a product gas stream containing an elevated proportion of methane and a gas stream containing a reduced proportion of methane. A quality sensor may be arranged in the outlet line for the highly pure product gas. A vacuum pump, the capacity of which can be regulated, may be connected to the low-pressure side of one of the membrane units. It is controlled by a control unit which receives its input signal from the quality sensor in the outlet line, and if the proportion of methane measured by the quality sensor falls below a certain value, the capacity of the vacuum pump is regulated so that the pressure difference at the membrane increases.

4 Claims, 1 Drawing Sheet

(56) References Cited

U.S. PATENT DOCUMENTS

2004/0168570 A1* 9/2004 Franek ................ 95/50
2005/0229778 A1 10/2005 Backhaus et al.
2007/0125537 A1* 6/2007 Lokhandwala et al. ...... 166/291
2011/0041687 A1* 2/2011 Diaz et al. ................ 95/51
2013/0098242 A1* 4/2013 Ungerank et al. ........... 95/51
2013/0109767 A1* 5/2013 Bogild Hansen ............. 518/702

FOREIGN PATENT DOCUMENTS

EP 1 324 815 5/2004
WO 2012/000727 A1 1/2012

* cited by examiner

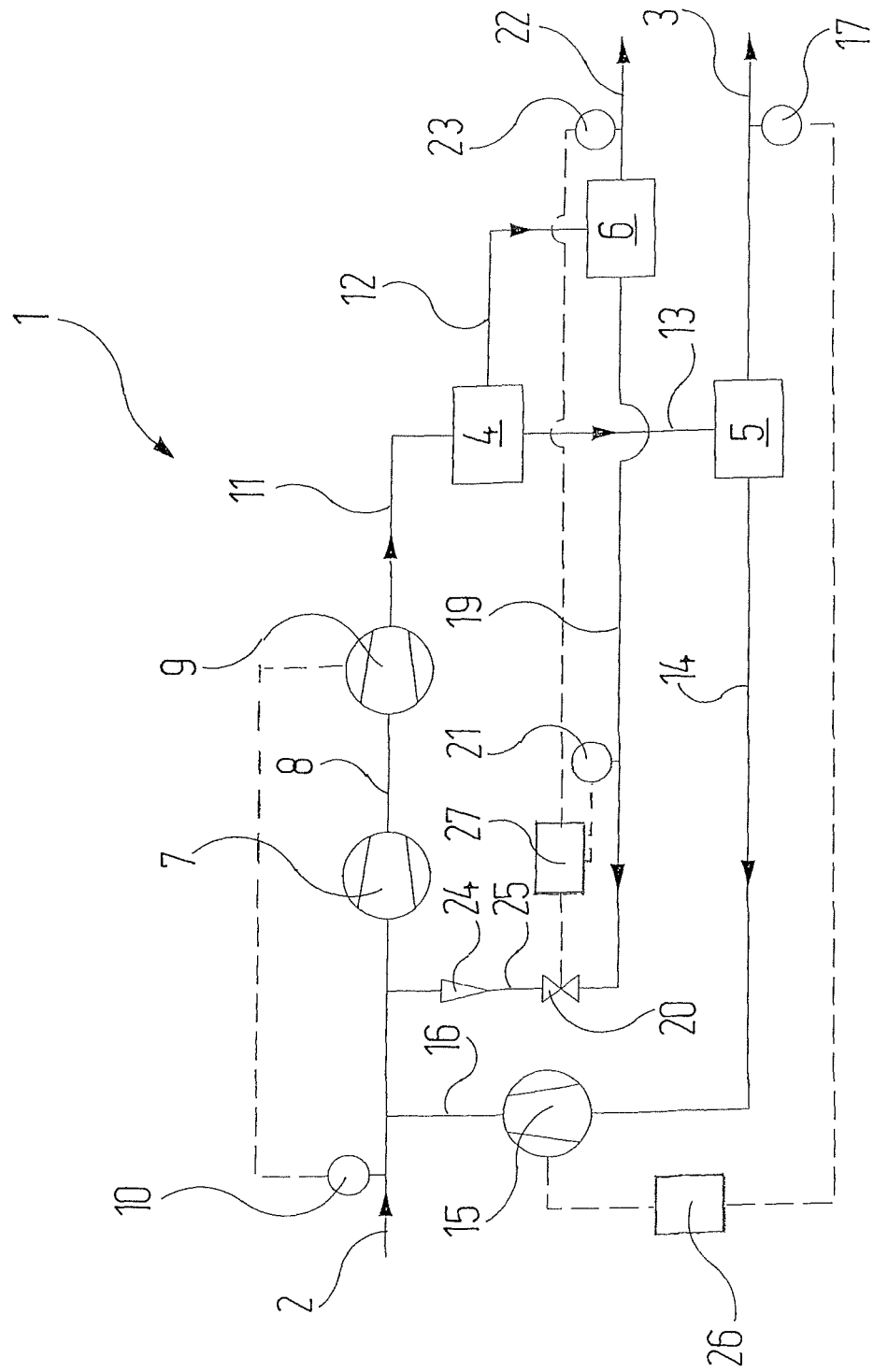

PROCESS FOR OBTAINING HIGHLY PURE METHANE FROM BIOGAS, AND PLANT FOR CARRYING OUT THE PROCESS

RELATED APPLICATIONS

This application claims priority to German Application No. 10 2013 004 079.5 filed Mar. 11, 2013, the contents of which is incorporated herein by reference.

TECHNICAL FIELD

The invention relates to a process for obtaining highly pure methane from biogas, in which
a) the biogas coming from a fermenter is compressed;
b) the compressed biogas is divided by means of at least one selectively permeable membrane into at least two gas streams, of which one contains an elevated proportion of methane and the other contains a reduced proportion of methane;
wherein
c) a pressure difference is generated at the membrane;
d) a gas stream containing a sufficient proportion of methane is fed as product gas to a further use;
and
to a plant for obtaining highly pure methane from biogas, having
a) a compressor in which the biogas coming from a fermenter is compressed;
b) at least one membrane unit which comprises:
  ba) an inlet for the gas mixture to be separated;
  bb) a selectively permeable membrane, one side of which is exposed to a higher pressure during operation and the other side of which is exposed to a lower pressure;
  bc) a retentate outlet on the high-pressure side of the membrane unit, via which a gas stream that contains an elevated proportion of methane can be removed;
  bd) a permeate outlet on the low-pressure side of the membrane unit, via which a gas stream that contains a reduced proportion of methane can be removed;
c) a first outlet line, via which a product gas stream consisting of highly pure methane can be fed to a further use;
d) a second outlet line, via which an offgas stream containing only a small proportion of methane can be discharged to the environment.

BACKGROUND OF THE INVENTION

Such a process and such a plant are known from WO 2012/000727 A1. That publication describes especially various connection arrangements of a plurality of membrane units with which a product gas that contains a very high proportion of methane can be achieved. At the same time, the offgas stream is to contain as small an amount of methane as possible. Although it is mentioned in that publication that the pressure difference at the selectively permeable membrane influences the selectivity thereof, no further use is made of that finding. Instead, the method chosen for increasing the selectivity of the process is a specific manner of recycling of gas streams. Permanent monitoring of the quality of the product gas, and in particular regulation to a specific proportion of methane therein, does not take place here.

In EP 1 324 815 B1 it is described, using the example of a plant that produces nitrogen of high purity, that the quality of the product gas can be monitored continuously by a sensor, the pressure difference at at least one membrane unit then being changed accordingly in order to ensure a specific product gas quality. This change takes place in EP 1 324 815 B1 by changing the speed of the compressor which compresses the fed gas mixture, that is to say on the high-pressure side of the membrane, which has the result that the volume flow passing through the plant changes in a readjustment process. This is generally less desirable.

SUMMARY OF THE INVENTION

An object of the present invention is to configure a process and a plant of the type mentioned at the beginning in such a manner that a specific quality of the product gas can permanently be maintained during operation, without the occurrence of appreciable changes in the volume flow during the regulating process.

As far as the process is concerned, the object may be achieved in that
e) the proportion of methane gas in the product gas is measured continuously;
f) if the proportion of methane in the product gas falls below a specified value, the pressure difference at a membrane is increased by generating a vacuum or increasing an existing vacuum on the low-pressure side of the membrane.

Conceptually, the invention thus follows part of the method outlined in EP 1 324 815 B1 for gases other than biogases: It provides a sensor which monitors the quality of the product gas that is produced. However, the change in the applied pressure difference that is required to change the selectivity of the selectively permeable membrane is effected not on the high-pressure side of the membrane but on the low-pressure side. This has the result that no appreciable changes in the volume flow occur in readjustment processes. The procedure according to the invention is surprising inter alia because far fewer changes in the pressure are understandably possible on the low-pressure side than on the high-pressure side. It has been found according to the invention that the possible pressure changes are sufficient for the desired regulating process in the production of highly pure methane.

As far as the plant is concerned, the object mentioned above may be achieved in that
e) there is provided in the first outlet line a first quality sensor which generates a signal representative of the proportion of methane in the product gas;
f) there is provided a vacuum pump which is connected on the suction side to the low-pressure side of a membrane unit and on the pressure side directly or indirectly to the inlet of the compressor;
g) there is provided a first control device to which the signal of the first quality sensor can be fed and the output signal of which regulates the suction capacity of the vacuum pump in such a manner that the proportion of methane in the product gas does not fall below a specified value.

The advantages of the plant according to the invention correspond analogously to the above-mentioned advantages of the process according to the invention.

In an embodiment of the invention, at least two membrane units are provided,
wherein
the inlet of the first membrane unit is connected to the outlet of the compressor;
the retentate outlet of the first membrane unit is connected to the inlet of the second membrane unit;
the vacuum pump is connected to the permeate outlet of the second membrane unit;
the retentate outlet of the second membrane unit is connected to the first outlet line for the product gas.

The interconnection of two membrane units arranged in series is known from WO 2012/000727 A1 mentioned above. It serves to produce a product gas that is more highly enriched with methane. Of interest in the present context, however, is the influencing according to the invention not of the first but of the second membrane unit by generating a vacuum on the low-pressure side.

Finally, particular preference is given to a plant having two membrane units, in which the permeate outlet of the first membrane unit is connected to the inlet of a third membrane unit, the retentate outlet of which is connected via a controllable regulating valve directly or indirectly to the inlet of the compressor and the permeate outlet of which is connected to the second outlet line for the offgas;
wherein
in the second outlet line for the offgas there is provided a second quality sensor which generates a signal representative of the proportion of methane in the offgas;
there is provided a second control unit to which the signal of the second quality sensor can be fed and the output signal of which controls the regulating valve in such a manner that a specified value for the proportion of methane in the offgas is not exceeded.

The interconnection of two membrane units in such a manner that the permeate connection of the first membrane unit is fed to the inlet of a further membrane unit again is likewise described in WO 2012/000727 A1. It serves to obtain methane that is still contained in the permeate of the first membrane unit and was otherwise lost. According to the invention, unlike in that publication, the product quality of the offgas is monitored, it being crucial that the proportion of methane does not become too high. However, regulation of the selectivity of the third membrane unit now necessarily takes place on the pressure side, but not by means of a change in the compressor speed but via a regulating valve which is opened further, the lower the desired pressure on the high-pressure side of the corresponding membrane.

It is to be understood that the aspects and objects of the present invention described above may be combinable and that other advantages and aspects of the present invention will become apparent upon reading the following description of the drawings and detailed description of the invention.

BRIEF DESCRIPTION OF THE DRAWINGS

An exemplary embodiment of the invention is described in greater detail below with reference to the drawing; the single FIGURE shows schematically the layout of a plant for obtaining highly pure methane from biogas.

DETAILED DESCRIPTION OF THE PRESENT INVENTION

While this invention is susceptible of embodiment in many different forms, there is shown in the drawings and will herein be described in detail one or more embodiments with the understanding that the present disclosure is to be considered as an exemplification of the principles of the invention and is not intended to limit the invention to the embodiments illustrated.

The plant shown in the drawing and provided generally with the reference numeral 1 for obtaining highly pure methane receives biogas, that is to say a mixed gas that consists substantially of nitrogen, oxygen, $CO_2$, CO and, of course, methane, from a fermenter (not shown) via a line 2. In the plant 1, substantially all the constituents of the biogas are separated off in a manner which will be described in greater detail below, with the exception of methane, which is discharged in highly pure form via a first outlet line 3. The quality of the methane discharged here is over 96%, especially over 98%, so that it can be introduced directly into a natural gas supply system if required. Negligible constituents of other gases that remain can be 2% $CO_2$ and/or 2% $N_2$, residual constituents which do not prevent the purified gas from being utilised in a natural gas system.

Purification of the biogas fed via the line 2 takes place with the aid of three membrane units 4, 5 and 6, which are connected together in a specific way which will be described below. The construction of the membrane units 4, 5, 6 is conventional and thus does not need to be described in greater detail. It is sufficient to know that each of the membrane units 4, 5, 6 has a selectively permeable membrane which separates a first chamber, to which the gas to be separated is fed via an inlet and from which the gas that permeates less easily (retentate) is removed via a retentate outlet, from a chamber in which the gas that permeates better (permeate) passes through the membrane and from which it is removed via a permeate outlet.

The retentate sides of the membrane units 4, 5, 6 are at a higher pressure than the permeate side; this pressure difference represents the "driving force" of the separation operation. It is known that the selectivity of the separation operation increases with the pressure difference prevailing at the membrane.

Following these preliminary comments, the detailed interconnection of the various membrane units 4, 5, 6 will now be explained.

The biogas fed via the line 2 is first fed to a fan 7, which is connected on the outlet side via a line 8 to a compressor 9. A pressure sensor 10 measures the pressure of the biogas in the line 2 and controls the speed of the compressor 9, that is to say its conveying capacity, proportionally.

The biogas compressed by the compressor 9 is then fed via the inlet to the first membrane unit 4; this takes place via a line 11. The permeate outlet of the first membrane unit 4 is connected via a further line 12 to the inlet of the third membrane unit 6. The retentate of the first membrane unit 4, on the other hand, is fed via a line 13 to the inlet of the second membrane unit 5. That membrane unit 5 is additionally connected on the permeate side, via a line 14, to the suction side of a vacuum pump 15, which feeds the permeate sucked in from the second membrane unit 5 to the line 2 again via a line 16 and is accordingly again fed, together with the biogas from the fan 7 flowing in via the line 2, to the right in the drawing to the compressor 9.

The retentate outlet of the second membrane unit 5 is connected to the first outlet line 3, with which there communicates a sensor 17 which measures the quality of the outflowing purified product gas. The sensor is preferably an optical sensor which is sensitive to methane. Such sensors are known and available commercially; they therefore do not need to be described in greater detail.

The output signal of the sensor 17 is fed to a first control device 26, which delivers an output signal which determines the suction capacity of the vacuum pump 15. In the line 14 which connects the permeate outlet of the second membrane unit 5 to the vacuum pump 15 there can additionally be located a pressure sensor (not shown), the output signal of which is likewise transmitted to the first control device 26 and the function of which will become clear later.

The remaining connections of the third membrane unit 6 will now be described:

The retentate of the third membrane unit 6 is fed via a line 19 to a regulating valve 20. A pressure sensor 21 monitors the pressure of the flow of retentate in the line 19.

The permeate of the membrane unit 6 is discharged as offgas via a second outlet line 22 and discarded. The quality of the offgas is monitored by a second quality sensor 23, which can be of the same type as the above-mentioned first quality sensor 17. In particular, therefore, it can be an optical sensor with sensitivity for methane. The output signals of the second quality sensor 23 and of the pressure sensor 21 are transmitted to a second control device 27, which can in principle be combined with the first control device 26 already mentioned above or with the higher-level plant control system and the output signal of which acts upon the regulating valve 20 in the manner described below.

On the output side, the regulating valve 20 is connected via a relief valve 24, which is located in a line 25, likewise to the input of the fan 7.

The functioning of the above-described plant 1 comprising three interconnected membrane units 4, 5, 6 is as follows:

The biogas removed from the fermenter is, as already mentioned, sucked in via the fan 7 and thereby mixes in steady-state operation of the plant 1 with gas which is recycled via the lines 16 and 25 from the second membrane unit 5 and the third membrane unit 6, respectively. The capacity of the compressor 9 is thereby determined by way of the pressure measured by the pressure sensor 10.

Gas mixture compressed by the compressor 9 passes to the inlet of the first membrane unit 4; the retentate, which is enriched with methane owing to the selectivity of the membrane used, is passed via the line 13 to the inlet of the second membrane unit 5, where a selective separation again takes place: The retentate of the second membrane stage 5, which in the required manner contains mainly methane, is the desired product gas and is fed via the first outlet line 3 to a natural gas supply system, for example.

The quality of that gas is monitored by the first quality sensor 17. If the quality falls below a desired value, the first control device 26, to which the signal of the quality sensor 17 is transmitted, ensures that the suction capacity of the vacuum pump 15 is increased. This has the result that the reduced pressure on the permeate side of the second membrane unit 5 increases, which in turn leads to better selectivity of the membrane located in the second membrane unit 5. The consequence is a better quality of the product gas on the first outlet line 3, which is recorded by the sensor 17. The sensor 17 then delivers a corresponding signal to the first control device 26, which keeps the suction capacity of the vacuum pump 15 at the value required to maintain the quality of the product gas.

As regards the pressure sensor (not shown) which is optionally present:

A specific minimum value can be specified for the reduced pressure on the permeate side of the second membrane unit 5, which is measured by this pressure sensor. If the measured value falls below that minimum value, it is no longer possible to increase the separating action of the second membrane unit 5 appreciably by further reducing the vacuum by means of the vacuum pump 15. In such a case, further membrane units must optionally be connected in parallel with the second membrane unit 5 or the operation of the plant 1 must be interrupted in order to be able to replace the membranes of the second membrane unit 5.

The third membrane unit 6 serves to utilise any methane still present in the permeate of the first membrane unit 4 as far as possible. If the second quality sensor 23 in the second outlet line 22 detects too high a methane content that would be lost, the pressure difference at the membrane of the third membrane unit 6 is increased with the aid of the regulating valve 20, that is to say its selectivity is improved. To that end, the pressure on the line 19, measured by the pressure sensor 21, is reduced accordingly.

The result of the regulating operations outlined above is that, on the one hand, only a very small amount of methane is lost into the outside atmosphere via the second outlet line 22 and, on the other hand, a high-quality product gas is obtained via the first outlet line 3, which product gas contains sufficient methane that it can be used further equivalently to natural gas.

It is to be understood that additional embodiments of the present invention described herein may be contemplated by one of ordinary skill in the art and that the scope of the present invention is not limited to the embodiments disclosed. While specific embodiments of the present invention have been illustrated and described, numerous modifications come to mind without significantly departing from the spirit of the invention, and the scope of protection is only limited by the scope of the accompanying claims.

The invention claimed is:

1. Process for obtaining highly pure methane from biogas comprising:
   a) compressing biogas coming from a fermenter;
   b) dividing the compressed biogas into at least two gas streams using at least one selectively permeable membrane, of which one contains an elevated proportion of methane and the other contains a reduced proportion of methane;
   wherein
   c) a pressure difference is generated at the at least one selectively permeable membrane; and
   d) a gas stream containing a sufficient proportion of methane is fed as product gas to a further use;
   and further wherein
   e) the proportion of methane gas in the product gas is measured continuously; and
   f) if the proportion of methane in the product gas falls below a specified value, the pressure difference at a membrane is increased by generating a vacuum or increasing an existing vacuum on the low-pressure side of the membrane.

2. Plant for obtaining highly pure methane from biogas comprising:
   a) a compressor in which the biogas coming from a fermenter is compressed;
   b) at least one membrane unit which comprises:
      ba) an inlet for the biogas to be separated;
      bb) a selectively permeable membrane, of which one side is exposed to a higher pressure during operation and the other side is exposed to a lower pressure;
      bc) a retentate outlet on the high-pressure side of the at least one membrane unit, via which a gas stream that contains an elevated proportion of methane can be removed;
      bd) a permeate outlet on the low-pressure side of the at least one membrane unit, via which a gas stream that contains a reduced proportion of methane can be removed;
   c) a first outlet line, via which a product gas stream consisting of highly pure methane can be fed to a further use;
   d) a second outlet line, via which an offgas stream containing only a small proportion of methane can be discharged to the environment;
   wherein e) the first outlet line has a first quality sensor which generates a signal representative of the proportion of methane in the product gas stream;

f) a vacuum pump is connected on the suction side to the low-pressure side of a membrane unit and on the pressure side directly or indirectly to an inlet of the compressor; and g) a first control device to which the signal of the first quality sensor can be fed and the output signal of which regulates the suction capacity of the vacuum pump in such a manner that the proportion of methane in the product gas does not fall below a specified value.

3. Plant according to claim 2, wherein at least two membrane units are provided, wherein an inlet of a first membrane unit is connected to an outlet of the compressor;

the retentate outlet of the first membrane unit is connected to an inlet of a second membrane unit;

the vacuum pump is connected to a permeate outlet of the second membrane unit;

a retentate outlet of the second membrane unit is connected to the first outlet line for the product gas.

4. Plant according to claim 3, wherein the permeate outlet of the first membrane unit is connected to an inlet of a third membrane unit, a retentate outlet of which is connected via a controllable regulating valve directly or indirectly to the inlet of the compressor and a permeate outlet of which is connected to the second outlet line for the offgas;

wherein in the second outlet line for the offgas there is provided a second quality sensor which generates a signal representative of the proportion of methane in the offgas;

there is provided a second control device to which the signal of the second quality sensor can be fed and the output signal of which controls the regulating valve in such a manner that a specified value for the proportion of methane in the offgas is not exceeded.

* * * * *